United States Patent [19]

Petrofsky

[11] Patent Number: 4,586,495
[45] Date of Patent: May 6, 1986

[54] THERAPY SYSTEM FOR ACUTE PATIENT CARE

[75] Inventor: Jerrold S. Petrofsky, Beavercreek, Ohio

[73] Assignee: Wright State University, Dayton, Ohio

[21] Appl. No.: 627,241

[22] Filed: Jul. 2, 1984

[51] Int. Cl.$^4$ .............................................. A61N 1/32
[52] U.S. Cl. ................................. 128/82.1; 128/25 B; 128/782; 272/125
[58] Field of Search ................. 3/1.1, 1.2, 2; 128/733, 128/421, 422, 423 W, 774, 779, 782; 272/116, 117, 125, 129

[56] References Cited

U.S. PATENT DOCUMENTS

| | | | |
|---|---|---|---|
| 3,911,910 | 10/1975 | Oesau | 128/82.1 |
| 3,929,335 | 12/1975 | Malick | 272/129 |
| 4,148,303 | 4/1979 | Cohen | 128/733 |
| 4,236,528 | 12/1980 | Stanec et al. | 128/782 X |
| 4,387,723 | 6/1983 | Atlee, III et al. | 128/782 X |
| 4,421,336 | 12/1983 | Petrofsky et al. | 280/252 |
| 4,436,099 | 3/1984 | Raftopoulos | 128/782 |
| 4,480,830 | 11/1984 | Petrofsky et al. | 128/423 W X |

Primary Examiner—Kyle L. Howell
Assistant Examiner—Francis J. Jaworski
Attorney, Agent, or Firm—Biebel, French & Nauman

[57] ABSTRACT

Apparatus and method for stimulating muscular activity in an acutely injured patient. A leg which is to be stimulated is strapped into a brace, and the leg muscles are stimulated to work isometrically against the brace. The effort exerted by the muscles is measured by load cells which generate feedback signals for a control computer. The computer adjusts the stimulation signals in accordance with the received feedback signals.

12 Claims, 15 Drawing Figures

FIG-2
FIG-3
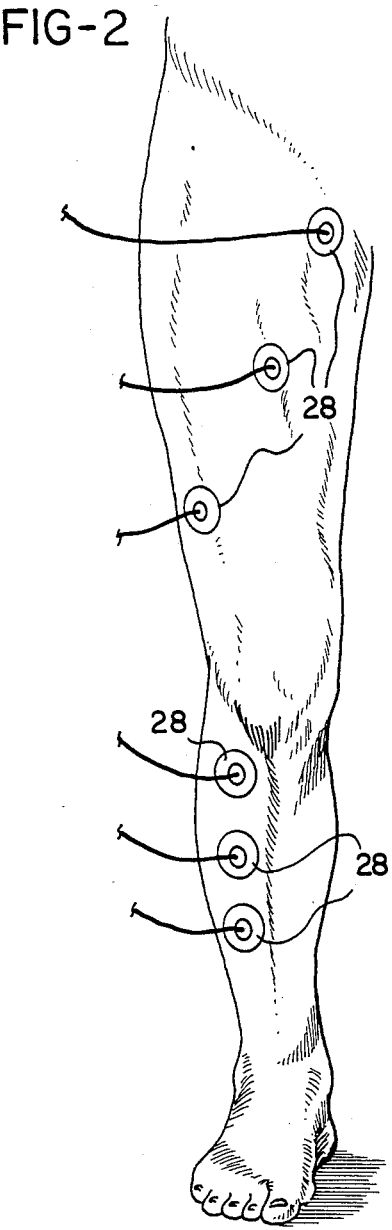
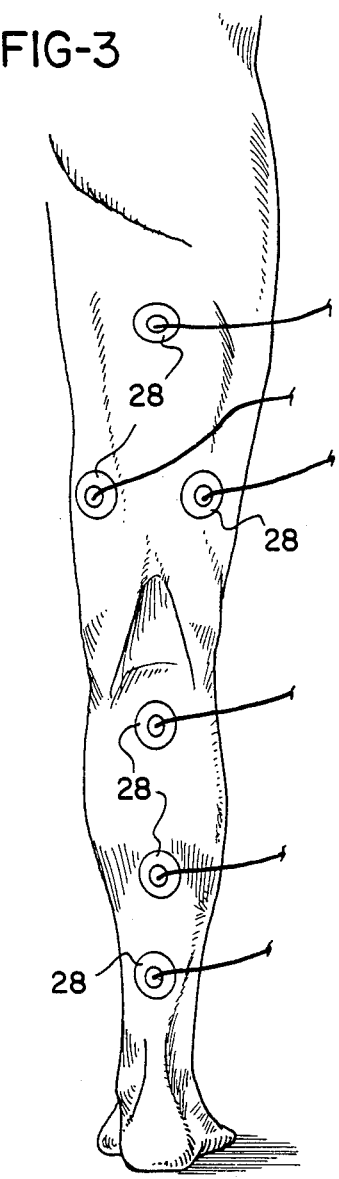

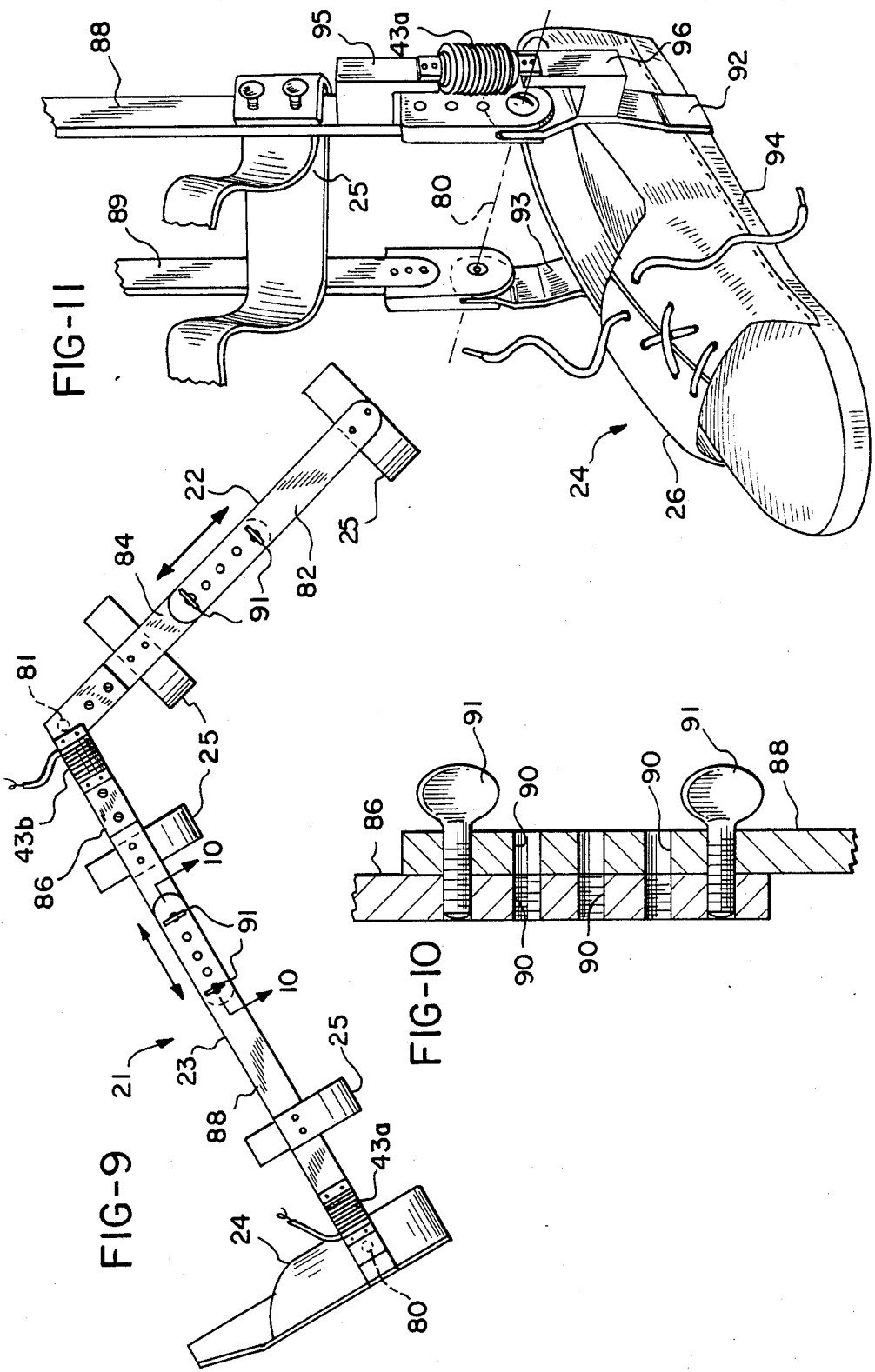

THERAPY SYSTEM FOR ACUTE PATIENT CARE

BACKGROUND OF THE INVENTION

This invention relates to a system for preventing physical deterioration of the muscles of severely injured patients. A serious injury may cause permanent spinal injury resulting in paraplegia or quadriplegia. The resulting prolonged disuse of the limbs produces atrophy of the muscles, deterioration of the tendons and osteoporosis in the bones. As the bones and muscles begin to decondition, there is a reduction in circulation of the blood, thereby predisposing the patient to pressure sores and blood clots.

It has been found that such physical deterioration can be reversed, even after years of muscular disuse, through a physical conditioning program based upon functional electrical stimulation of the paralyzed muscle. Typical apparatus for producing appropriate muscular stimulation is disclosed in Petrofsky et al U.S. Pat. No. 4,421,336 and includes pairs of alternately pulsed electrodes which may be applied to the surface of the skin above those muscles which are to be stimulated. Such stimulation devices have been used to stimulate operation of wheelchairs, tricycles, exercise bicycles and exercise chairs equipped with leg weights. Such systems have produced remarkable rehabilitation of long term paraplegic and quadriplegic patients.

It is known that the effects of muscle disuse begin to manifest themselves almost immediately upon cessation of muscular activity. The above-described prior art devices may be used only by persons who have recovered from the trauma of their injury and have regained a relatively stable physical condition. In the interim, however, such persons may have experienced a long period of physical inactivity during which muscular deterioration has commenced. If the injured person is in a state of coma, the inactivity may continue for many months. It is therefore seen that there is a need for a system to provide physical therapy for such acutely injured persons prior to the time when use of the above-mentioned prior art devices becomes appropriate.

SUMMARY OF THE INVENTION

This invention provides apparatus and method for preventing muscular deterioration in a spinal cord patient during the period of time following the spinal cord injury and prior to the period when stimulated dynamic exercise may be commenced. Apparatus in accordance with the invention includes means for stimulating a muscle to be exercised and restraining means for restraining movement of a joint activated by that muscle. The system further includes load selection means for selecting a target load for the muscle and a controller for controlling the operation of the stimulation means.

The controller causes the stimulation means to stimulate the muscle at the required level for causing an effort near the selected target load. Since the system restrains movement of the joint, the net result is a loading of the muscle which is isometric. The loading is maintained for a predetermined period of time, after which the muscle is rested. The entire cycle is repeated until a predetermined routine has been completed or the muscle has become exhausted.

In the preferred embodiment the restraining means comprises a leg brace having load cells which maintain the knee and the ankle at predetermined angles and provide feedback signals indicating the loading which has been achieved. The system alternately stimulates and rests agonist and antagonist muscles for each joint.

BRIEF DESCRIPTION OF THE DRAWINGS

FIG. 2 illustrates electrode attachment points at the front of the leg;

FIG. 3 illustrates electrode attachment points at the rear of a leg;

FIG. 9 is a side elevation view of a leg brace;

FIG. 10 is a view taken along lines 10—10 of FIG. 9;

FIG. 11 is an enlarged pictorial illustration of the lower end of a leg brace;

DESCRIPTION OF THE PREFERRED EMBODIMENT

Figure 1:
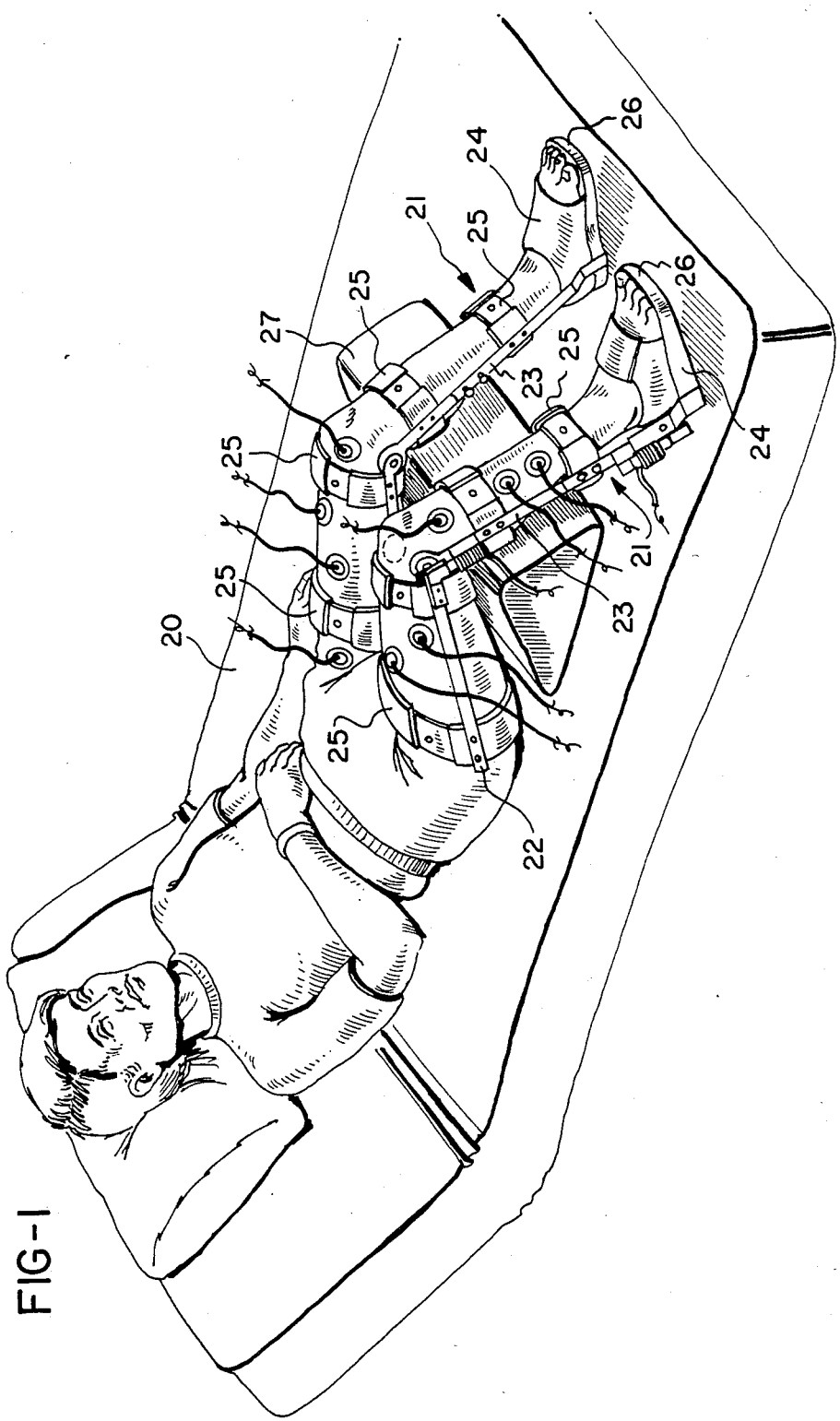
FIG. 1 is a pictorial illustration of an injured person undergoing therapy in accordance with this invention.

Physical therapy in accordance with this invention may be carried out as generally illustrated in FIG. 1. An injured person, who may be completely unconcious, rests on a bed 20 with his legs strapped in a pair of articulated braces 21, 21. As hereinafter described, only one brace is functional at any given time, so it is quite feasible to use only a single leg brace 21 and to change it from one leg to the other.

Leg braces 21 and 21 each consist of an upper leg portion 22, a lower leg portion 23 and a foot portion 24. A series of straps 25 and a pair of shoes 26, 26 are provided for securing leg braces 21, 21 to the legs of the patient. The leg braces maintain the legs of the patient with his knees slightly bent. Therefore, a rest 27 of triangular cross section is provided.

During the practice of this invention 24 electrodes 28 may be applied to the legs of the patient as illustrated generally in FIG. 1 and more particularly in FIGS. 2 and 3. These electrodes are applied in groups of three over agonist and antagonist muscles for the knee and ankle joints of each leg. Electrodes 28 are transcutaneous electrodes of the type set forth in TABLE II hereof. These electrodes are attached to the surface of the skin as described in Petrofsky et al U.S. Pat. No. 4,421,336. They are placed at locations for providing stimulation access to the muscles connected for causing movement of a joint to be loaded. The muscles stimulated by the illustrated electrode placement are the hamstring, quadriceps, tibialis anterior and gastrocnemius muscles of each leg. The hamstring and quadriceps muscles function as agonist and antagonist muscles respectively for the knee joint while the tibilias anterior and gastrocnemius muscles function as agonist and antagonist muscles, respectively, for the ankle joint.

In the embodiment as illustrated and as hereinafter described, the quadriceps muscles are stimulated for approximately four seconds to cause extending action of the knee against the restraining action of the leg brace. Thereafter, the quadriceps muscles are rested and the hamstring muscles are stimulated for a four second period to cause flexing of the knee against the restraining action of the leg brace. Thereafter, the hamstring muscles are rested for a four second period while continuing the resting action of the quadriceps muscles. The sequence is continually repeated, so that each muscle group exercises for four seconds, rests for eight seconds, and then exercises again. Since the leg braces permit only imperceptably small movement, an isometric exercise routine is achieved.

After the hamstring and quadriceps muscles have been exercised, the control system is connected for stimulating the tibialis anterior and gastrocnemius muscles of one leg. This causes controlled loading of those muscles against the restraining action of the leg brace at the ankle joint. The same stimulation sequence is performed as described above in connection with the hamstring and quadriceps muscles. Thereafter, the control system may be connected to the electrodes which stimulate muscular activity in the other leg.

As hereinafter described in detail the system measures the effort exerted by the stimulated muscles and compares this effort against a target load. The difference between the actual effort and the target load is utilized for adjusting the stimulation signals. In this manner the muscles may be stimulated to work isometrically at a precisely determined level of effort.

Figure 4:
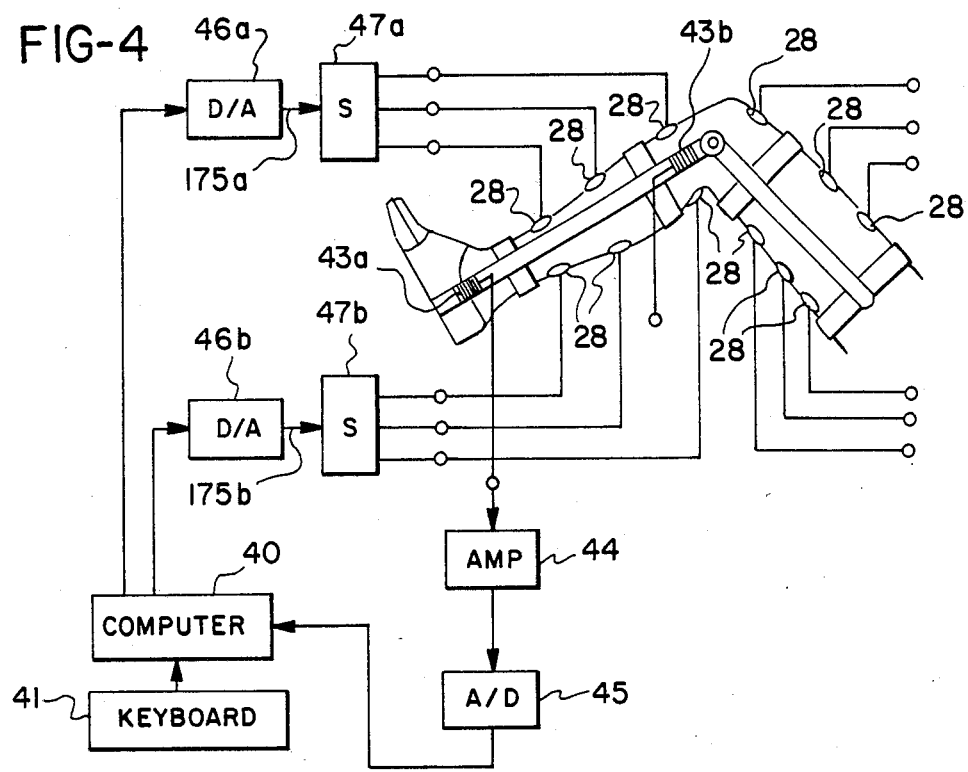
FIG. 4 is a schematic block diagram of the electrical components comprising the invention.

FIG. 4 presents a block diagram of the electrical controls for the system. The heart of the system is a programmed computer 40, which may be an APPLE II PLUS computer manufactured by Apple Computer Inc. of Cupertino, Calif. Computer 40 includes a keyboard 41 which permits entry of control commands. In particular, keyboard 41 is utilized for entry of target loads, as hereinafter described.

The electrical control system also includes a pair of load cells 43a, 43b for alternate selective usage. As shown in FIG. 4 load cell 43a is connected for computer control of muscular activity at the ankle joint. Output signals from load cell 43a are amplified by amplifier 44 and digitized by A/D converter 45. These output signals function as feedback signals, which computer 40 compares against input data from keyboard 41 to generate stimulation control signals. The stimulation control signals, so generated, are applied to a pair of D/A converters 46a, 46b for conversion to analog form. The analog signals then are applied to stimulation generators 47a, 47b which generate stimulation voltages for application to electrodes 28.

Figure 5:
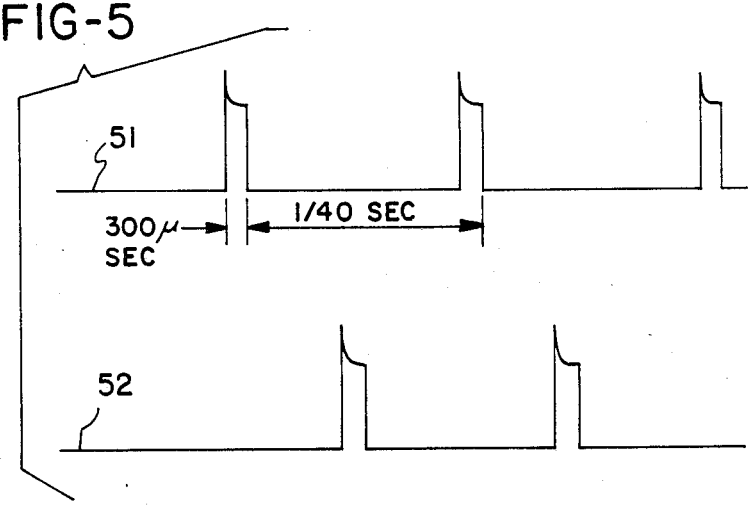
FIG. 5 is a schematic illustration of a stimulation waveform.

The waveform for the signals generated by stimulation generators 47 is illustrated in FIG. 5. That figure illustrates two signals 51 and 52. As described above, the stimulation electrodes are connected for operation in sets of three. The center electrode of each set is grounded. Signal 51 of FIG. 5 represents the voltage between the center electrode and one of the other two electrodes. Signal 52 represents the voltage between the center electrode and the third electrode of the set. Each signal comprises a series of pulses having a pulse width of about 300 microseconds generated at a frequency of 40 pulses per second.

Figure 6:
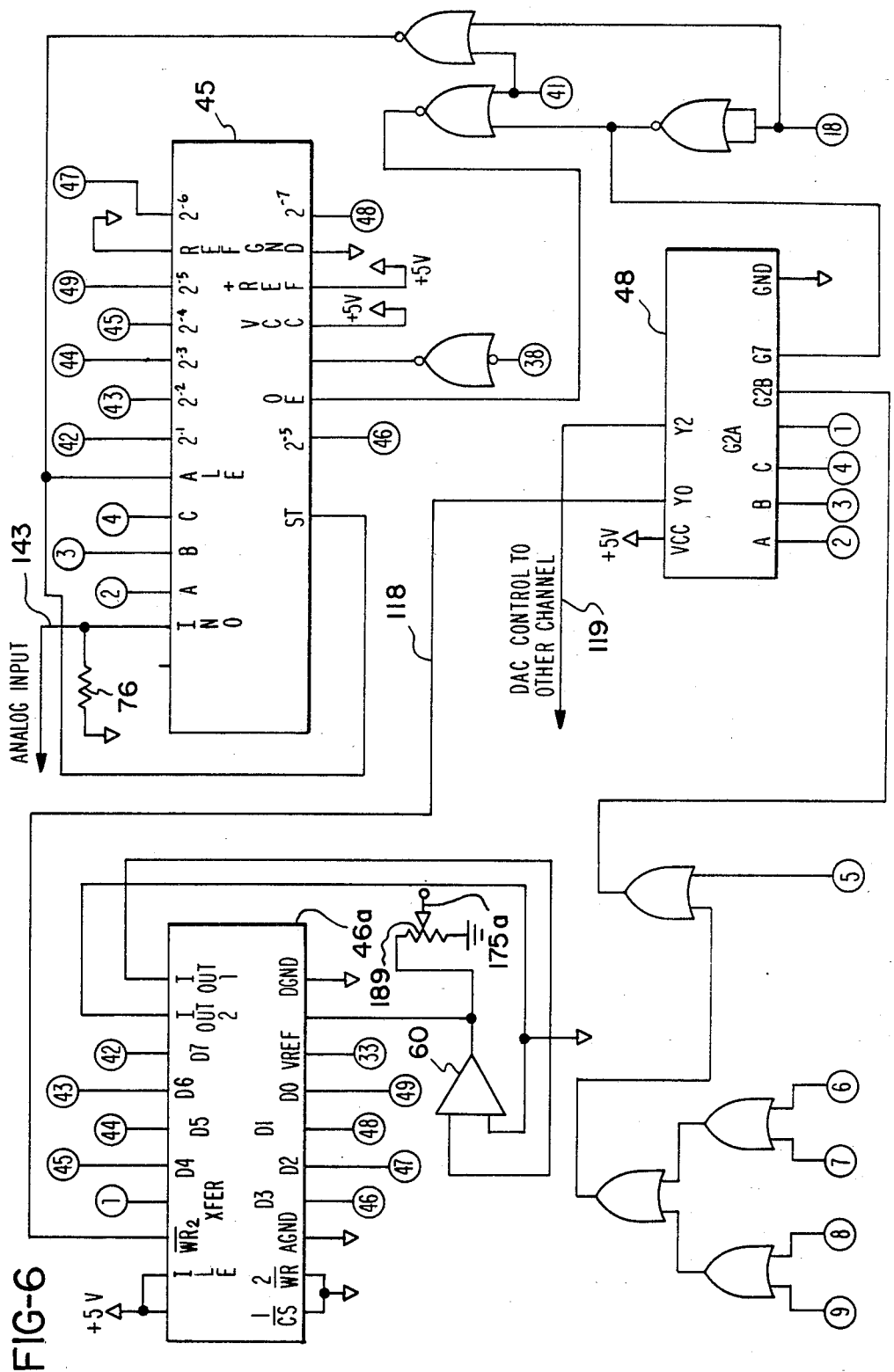
FIG. 6 is a schematic diagram of computer pin connections.
Figure 7:
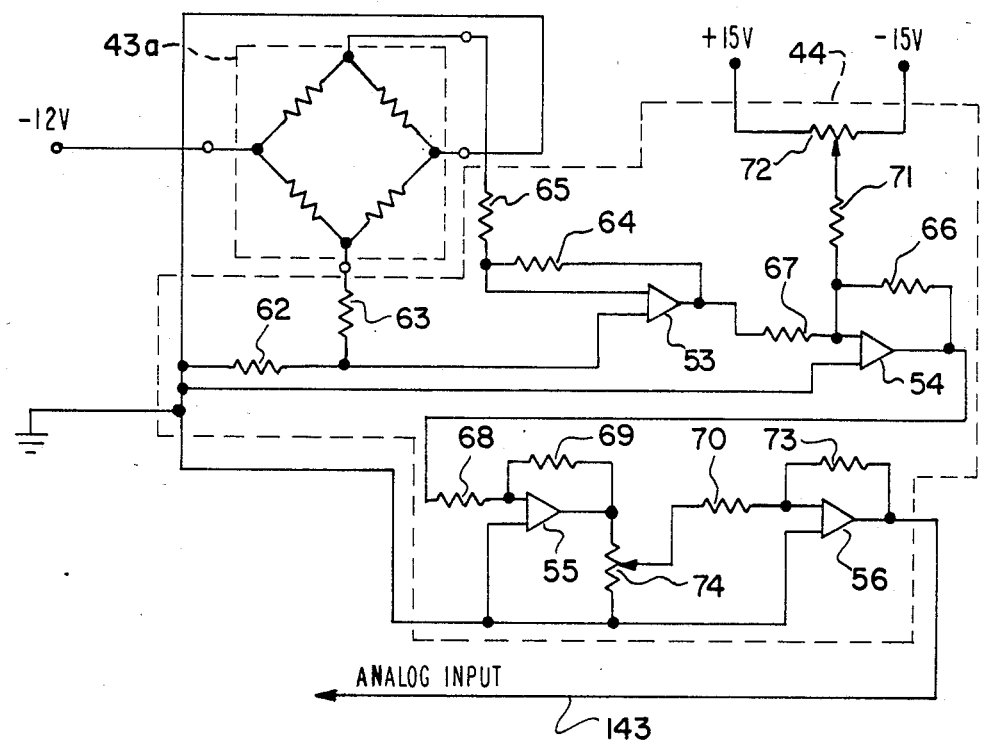
FIG. 7 is a schematic diagram of feedback elements.
Figure 8:
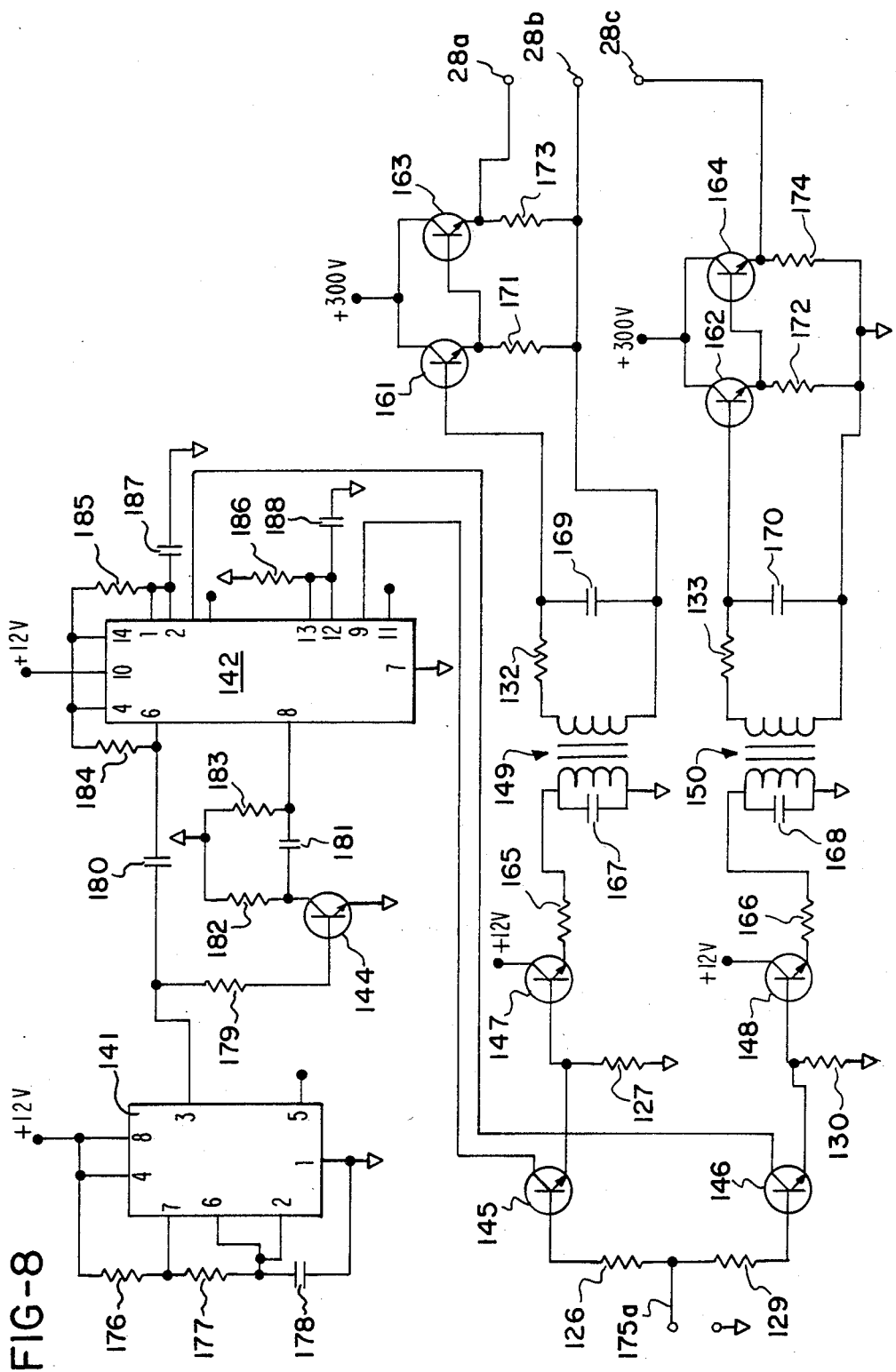
FIG. 8 is a schematic diagram of a stimulator.

FIG. 6 illustrates the details of the connections between the Apple Computer, A/D converter 45 and D/A converter 46a. The connections to D/A converter 46b are similar and are not illustrated in detail. Connection to the Apple Computer is made via a peripheral connector which plugs into peripheral slot 3 of the Apple Computer. Pin numbers for the connector are set forth on FIG. 6 and are encircled. TABLE I identifies the functions for each of the illustrated pins. The integrated circuits illustrated in FIG. 6, as well as all components of FIGS. 6–8 are identified in TABLE II.

TABLE I

| Pin No. | Function | Pin No. | Function |
| --- | --- | --- | --- |
| 1 | I/O SEL | 18 | R/W |
| 2 | A0 | 43 | D6 |
| 3 | A1 | 44 | D5 |
| 4 | A2 | 45 | D4 |
| 5 | A3 | 46 | D3 |
| 6 | A4 | 47 | D2 |
| 7 | A5 | 48 | D1 |
| 8 | A6 | 49 | D0 |
| 9 | A7 | | |

TABLE II
IDENTIFICATION OF ELECTRICAL COMPONENTS

| Reference Numeral | Identification |
| --- | --- |
| 28 | 3793 (Medtronic, Inc.) |
| 40 | APPLE II PLUS (Apple Computer) |
| 43a, 43b | 500 N wt. Load Beam (BLH Electronics) |
| 44 | 3178 (Daytronic Corp.) |
| 45 | ADC 0808 (National Semiconductor) |
| 46a, 46b | DAC 0832 (National Semiconductor) |
| 48 | SN 74LS138 (Texas Instrument) |
| 53, 54, 55, 56 | LM 1458 Op. Amp. |
| 60 | LM 1458 |
| 62–70 | 100K $\Omega$ |
| 71 | 1K $\Omega$ |
| 72 | 10K $\Omega$ |
| 73 | 1 Meg $\Omega$ |
| 74 | 10K $\Omega$ |
| 76, 77 | 100K $\Omega$ |
| 78 | 82K $\Omega$ |
| 126 | 1K $\Omega$ |
| 127 | 2.7K $\Omega$ |
| 129 | 1K $\Omega$ |
| 130 | 2.7K $\Omega$ |
| 132 | 2.7K $\Omega$ |
| 133 | 2.7K $\Omega$ |
| 141 | SE/NE 555 (Signetics) |
| 142 | SE/NE 556 (Signetics) |
| 144 | 2N3904 |
| 145 | 2N3904 |
| 146 | 2N3904 |
| 147 | TIP 31 |
| 148 | TIP 31 |
| 161 | E13004 |
| 162 | E13004 |
| 163 | E13004 |
| 164 | E13004 |
| 165 | 10$\Omega$ |
| 166 | 10$\Omega$ |
| 167, 168 | 0.05 $\mu$f |
| 169, 170 | 300 pf |
| 171–174 | 100K $\Omega$ |
| 176 | 1K $\Omega$ |
| 177 | 180K $\Omega$ |
| 178 | 0.1 $\mu$f |
| 179 | 10K $\Omega$ |
| 180, 181 | 680 pf |
| 182 | 2.7K $\Omega$ |
| 183, 184 | 10K $\Omega$ |
| 185, 186 | 2.7K $\Omega$ |
| 187, 188 | 0.1 $\mu$ |
| 189 | 5K $\Omega$ |

Decoder 48 decodes signals from computer 40 calling for output stimulation commands to be directed to one or the other of D/A converters 46a or 46b. The selection is made by the generated address of one or the other of the instructions POKE 49920, I1 or POKE 49922, I2. (See the complete program listing set forth in TABLE III). When these instructions are executed the decoder 48 transmits a write enabling command on one or the other of lines 118 or 119 for enabling D/A converter 46a or 46b. The selected D/A converter then causes an analog equivalent of I1 or I2 to appear on one or the other of lines 175a or 175b. Potentiometer 189 provides means for stimulation threshold adjustment as hereinafter described.

Reading of analog feedback signals from load cells 43a or 43b is initiated by execution of the instruction POKE 49328,0. This enables A/D converter 45 to read and digitize any analog signal which may be present on line 143. That line may be connected alternatively to one or the other of load cells 43a or 43b, depending upon the joint which has been selected for exercising. Reading of the digitized feedback signal is accomplished by execution of the instruction D=PEEK (49328).

Load cell 43a is a commercially available device, as listed in TABLE I, and the output thereof is applied to amplifier 44 which is also commercially available. The internal details of amplifier 44 are illustrated in FIG. 7 as including four amplifier stages comprising operational amplifiers 53 through 56 and associated resistors. Amplifier 53 provides a gain of 10, while amplifier 54 is connected for use as a balancing amplifier. Thus one input terminal of amplifier 54 is connected to a ten turn potentiometer 72 which is adjusted to produce a 2.5 volt output for a zero load output from load cell 43a. Amplifiers 55 and 56 each provide factor-of-ten gains. A potentiometer 74 provides gain adjustment.

Analog control signals on line 175a are processed by stimulator 47a through use of circuitry which is illustrated in detail in FIG. 8. Stimulator 47b is of identical construction and is not illustrated in detail. Stimulator 47a includes two integrated timing circuits 141 and 142. IC 141 is connected to operate as a 40 Hz free-running multivibrator. The output of IC 141 is applied to input pins 6 and 8 of IC 142. IC 142 produces alternating 300 microsecond pulses each at a frequency of 40 Hz for application to the collector terminals of transistors 145 and 146. The pulse width is set by an appropriate selection of the resistance for resistor 185 and the capacitance of capacitor 187, as shown in the manufacturer's data sheets for integrated circuit 142.

The analog control voltage generated on line 175a by D/A converter 46a is applied to the base terminals of transistors 145 and 146. Concomitantly, output pulses from pins 5 and 9 of IC 142 are applied to the collectors of transistors 146 and 145, respectively. As a result thereof, transistors 146 and 145 generate emitter currents across resistors 130 and 127 providing voltage profiles of the general shape illustrated in FIG. 5. These voltages are applied to the base terminals of transistors 148 and 147 for generating voltage pulses ranging between 0 to 12 volts across the primary windings of transformers 150 and 149.

The voltage pulses across the primary windings of transformers 150 and 149 produce low current, high voltage pulses ranging from 0 to 60 volts across the secondary windings of transformers 150 and 149. The secondary windings of transformers 150 and 149 have one side grounded to a high voltage ground which is different from the ground utilized for the primary windings thereof. The output pulses from the secondary windings are thereby RF isolated to maintain the safety of the paralyzed person.

Output voltages from transformers 150 and 149 are used for driving transistor pairs 162, 164 and 161, 163, respectively. Transistor pairs 162, 164 and 161, 163 provide a current gain so as to have high current, high voltage and low duty cycle pulses available for application across electrode pairs 28b, 28c and 28b, 28a. The signals across the two terminal pairs are represented by signal lines 51 and 52, respectively, of FIG. 5.

FIG. 9 illustrates the construction details of a typical brace 21. As described above, brace 21 includes an upper leg portion 22, a lower leg portion 23 and a foot portion 24. Upper leg portion 22 and lower leg portion 23 are joined along a pivot line 81. Pivotal motion therebetween is substantially restrained, however, by load cell 43b as more fully illustrated in FIGS. 12 and 13. Lower leg portion 23 and foot portion 24 are joined along another pivot line 80. Pivotal motion about pivot line 80 is substantially restrained by load cell 43a as illustrated in FIG. 11.

Upper leg section 22 of a leg brace 21 comprises four longitudinally extending framing rods 82 through 85, and lower leg section 23 comprises four longitudinally extending framing rods 86 through 89. Framing rods 82, 84, 86 and 88 are on that side of leg brace 21 facing load cells 43a and 43b and therefore are visible in FIG. 9. Framing rods 83, 85, 87 and 89 are on the opposite side of leg brace 21 and therefore are not visible in FIG. 9. The framing rods are assembled in pairs in overlapping relationship as illustrated generally in FIG. 9 and more particularly in FIG. 10. The framing rods are provided with a series of mating apertures 90 which are threaded for reception of thumb screws 91. This provides means for adjusting the length of leg sections 22 and 23.

As best illustrated in FIG. 11, framing rods 88 and 89 are pivotally joined to a pair of steel straps 92 and 93, which in turn are secured to the sole 94 of shoe 26. Load cell 43a is supported by a pair of support members 95 and 96, which are mounted upon framing rod 88 and strap 92, respectively.

In operation, shoe 26 is laced securely to the foot of the patient, so that when the ankle muscles are stimulated the foot produces a torque about hinge line 80. Sole 94 of shoe 26 is of rigid construction, so that the torque so produced is transmitted through strap 92 and support member 96 to load cell 43a. Load cell 43a is of relatively rigid construction so that there is no perceptable rotation of shoe 26 about hinge line 80. There is, however, a very slight rotation which is sensed by a resistance bridge arrangement within load cell 43a (see FIG. 6) and converted into an electrical indication of load.

Figure 12:
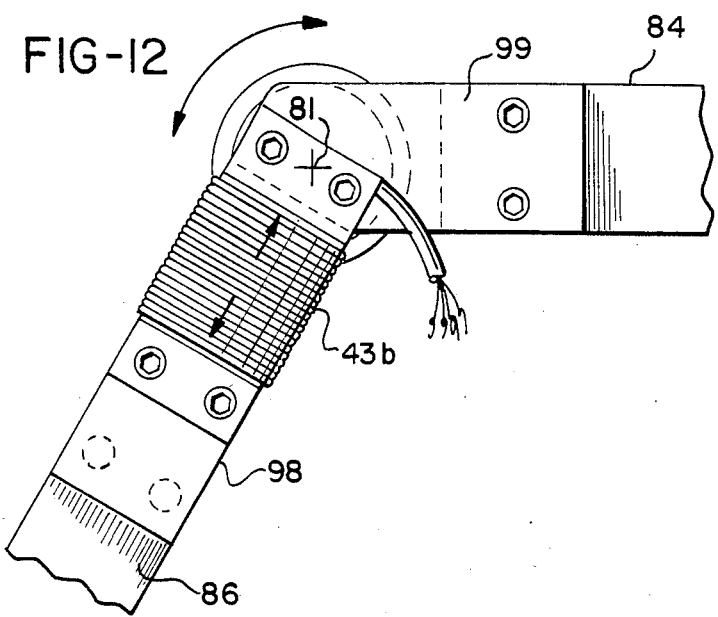
FIG. 12 is an enlarged view of that portion of a leg brace at the knee joint, as seen in side elevation.
Figure 13:
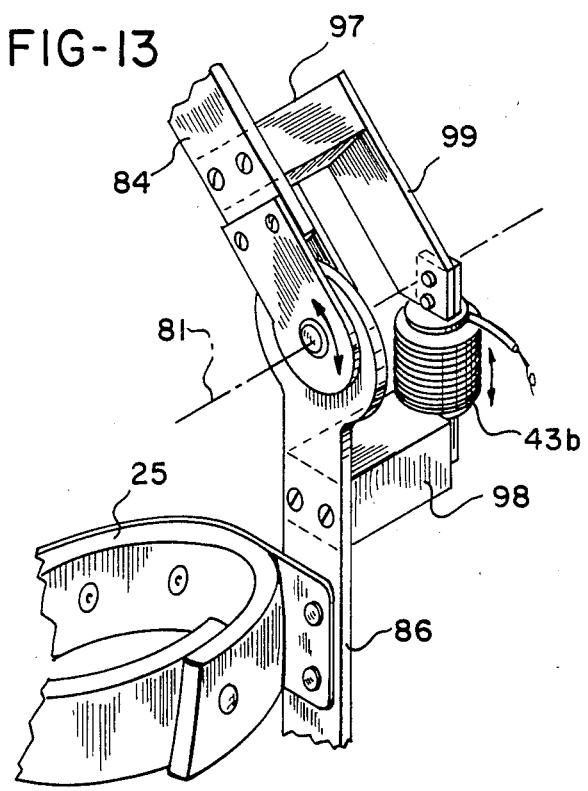
FIG. 13 is a perspective view of that portion of a leg brace shown in FIG. 12.

The mounting of load cell 43b is similar to the mounting of load cell 43a, as may be seen by reference to FIGS. 12 and 13. Load cell 43b is supported by mounting blocks 97 and 98 which are secured to rod members 84 and 86, respectively. There is a support member 99 secured to mounting block 97, and load cell 43b is mounted between support member 99 and mounting block 98. This prevents any significant rotary motion between framing rods 84 and 86. Thus angular movement of the knee is restrained when the knee muscles are stimulated.

Figure 14A:
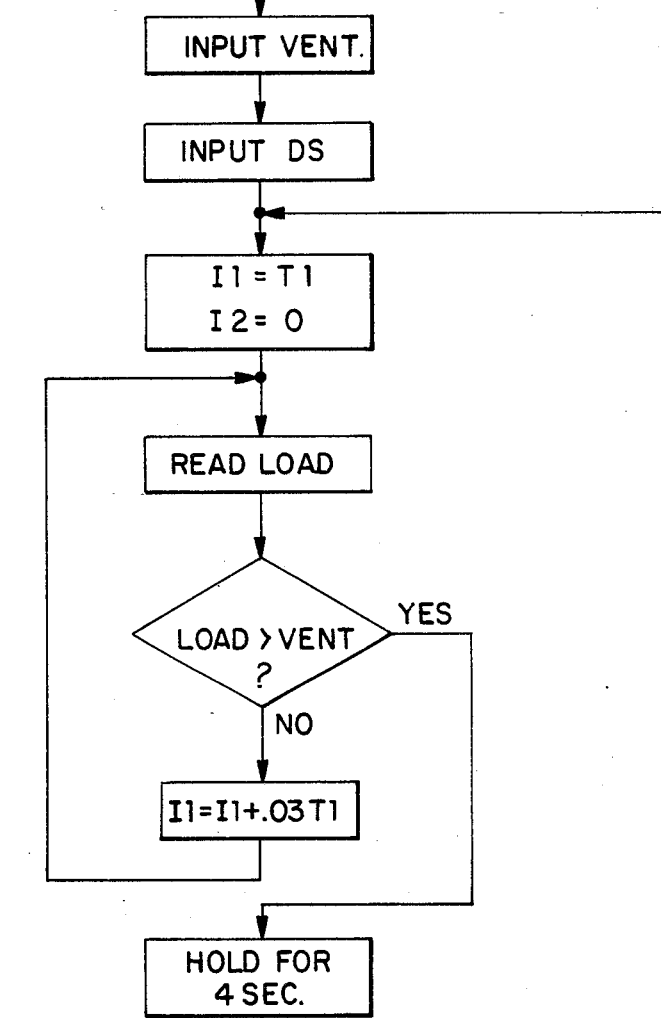
FIGS. 14A and 14B are a flow chart for portions of a computer program for carrying out the present invention.
Figure 14B:
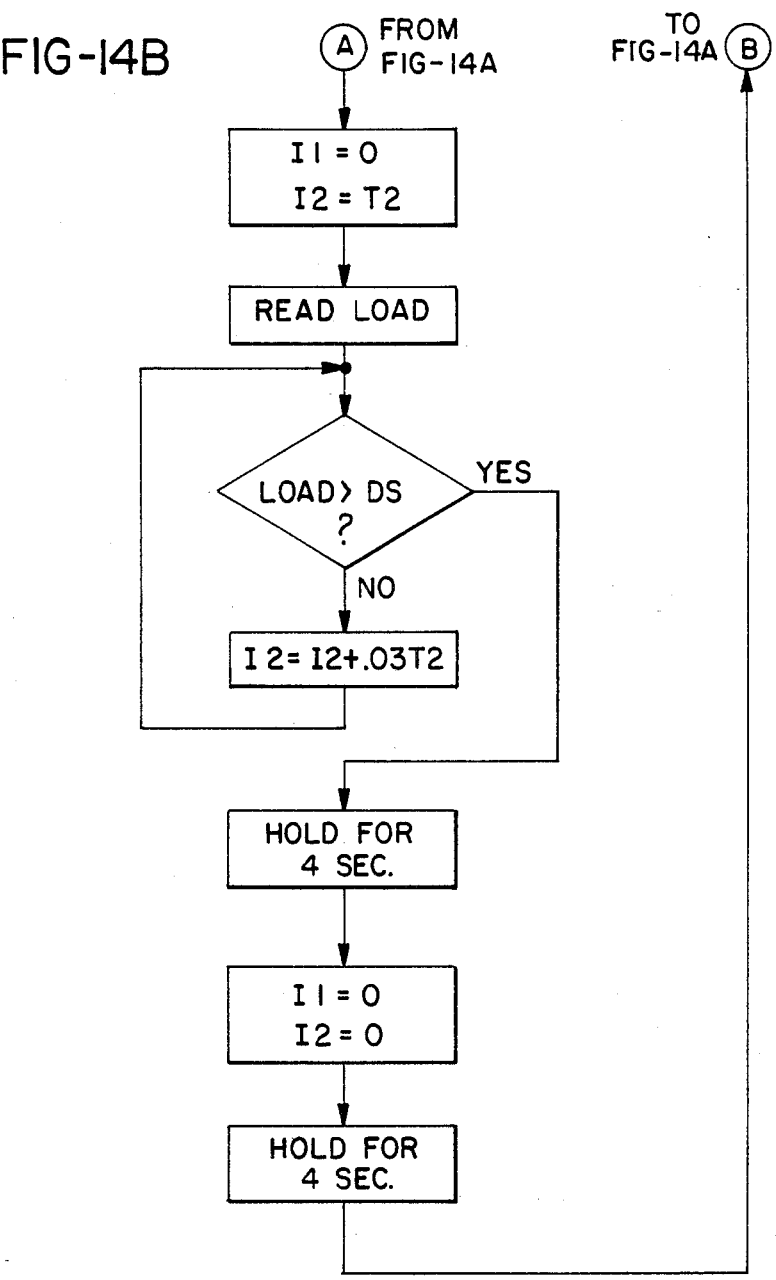

The operation of computer 40 will now be described with reference to the flow chart of FIGS. 14A and 14B and the program listing of TABLE III. The program as set forth in TABLE III is written in APPLESOFT, a form of the BASIC language adapted for operation on an APPLE II PLUS computer. This is a relatively high level source language, and the program listing is therefore self-explanatory. However, some comments are appropriate.

The program begins with a series of instructions related to load cell calibration. During this part of the program the display monitor provides instructions directing the operator to disconnect the operative load cell from leg brace 21 and to suspend a reference weight (5 lbs.) therefrom. Prior to attachment of the weight, however, balance potentiometer 72 is adjusted under zero load conditions until a value of 125 units is read on the computer monitor. The program loops between steps 700 and 800 while this adjustment is made. After the adjustment is made, the operator may press any key of keyboard 41 to cause an exit from the looping routine. Thereafter, the operator is instructed to place a 5 lb. load on the sensor and input a scale factor through keyboard 41. The scale factor corresponds to the sensitivity of load cell 43a in terms of volts per pound. This factor is established prior to the therapy routine and is marked on the equipment. The factor may be established rather easily by running the program in the laboratory with an added loop to permit trial and error variation of both the input scale factor and the adjustment of potentiometer 74. In such a procedure potentiometer 74 is set to a mid-range value, and the scale factor is varied between 1 and 10 until a value near 5 lbs. is obtained. Then potentiometer 74 is adjusted until a reading of exactly 5 lbs. is obtained. The computer obtains the weight reading as shown at program steps 1020 to 1040 by examining the voltage value stored in location 49328, adjusting for the zero load value, and then applying the scale factor.

After calibration has been completed, then the stimulation threshold is set for both the ventral and dorsal muscles. This setting is accomplished through use of potentiometer 189 in each stimulation channel, as documented at program steps 1300 through 1860. For each muscle the potentiometer is adjusted from a zero position up to another position where the muscle begins to twitch. Threshold settings are established while the computer is transmitting the hexadecimal equivalent of the decimal number 64 to D/A converters 46a and 46b.

Thereafter, the computer uses the number 64 as the value for threshold stimulation voltage.

After threshold setting has been completed the attending physician checks the patient and prescribes target loads for the ventral and dorsal muscles. These target loads may have any value up to 30 lbs. and are input to the computer at program step 3150 as variables VENT and DS. Keyboard 41 is used for this input.

After the target loads have been read into the computer the stimulation sequence commences. The steps for that sequence are outlined in the flow chart of FIGS. 14A and 14B. As noted in the flow chart the computer begins by setting the ventral stimulation at the threshold value and setting the dorsal stimulation at 0. The ventral stimulation then is increased stepwise until the target value has been reached. The target value is held for four seconds, following which the ventral stimulation is set to zero and the dorsal stimulation is set at a value equal to its target load. Thereafter, the dorsal stimulation is increased stepwise to its target value and held for four seconds. Following this, both muscles are rested for four seconds and the entire sequence is repeated. The routine produces periodic isometric loading of the stimulated muscles.

As the routine progresses the muscles will begin to tire, and the feedback signal from the load cell will begin to decrease. The computer compensates for this decrease by increasing the stimulation level until a maximum value of 200 units is reached (corresponds to 50 volts). No further voltage increases are made beyond that point. The routine is terminated at any time by depressing any key of keyboard 41. The computer senses the depression of the key at one or the other of program steps 3350 or 3450. The program then discontinues all stimulation and awaits an instruction to recommence, if desired. Stimulation may be resumed by typing the letter R, as noted at program step 3240.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

TABLE III

```
 1    FELAY = 2000
 2    REM   SET FELAY FOR DELAY ON FIRST SCREEN
 3    REM   ****ACUTE PATIENT STUDY****
 4    REM   ****        JSP *******
 5    REM   ****NAME OF PROGRAM IS ACUTE****
 6    MAX = 100:  REM   THIS IS THE MAX THRESHOLD
 8    FOR I = 1 TO 10:  PRINT :  NEXT I
10    PRINT "ACUTE SPINAL CORD INJURY PROGRAM"
20    PRINT :  PRINT :  PRINT :  PRINT
30    PRINT "          WSU NCRE           "
40    PRINT :  PRINT :  PRINT :  PRINT
50    PRINT :  PRINT :  PRINT
60    FOR I = 1 TO FELAY: NEXT I
70    FOR I = 1 to 20:  PRINT :  NEXT I
80    PRINT "TURN STIMULATOR HIGH VOLTAGE OFF"
```

```
90   PRINT : PRINT: PRINT "TYPE E WHEN READY"
100  PRINT : PRINT: PRINT : PRINT: PRINT : PRINT
110  INPUT A$
120  IF A$ = "E" THEN GOTO 200
130  PRINT "ERROR RETYPE"
135  GOTO 110
200  PRINT
210  FOR I = 1 TO 30: PRINT : NEXT I
220  PRINT "TEST SENSOR"
230  PRINT : PRINT : PRINT : PRINT : PRINT : PRINT : PRINT : PRINT : PRINT
240  FOR I = 1 TO FELAY: NEXT I
250  FOR I = 1 to 30: PRINT : NEXT I
270  PRINT "IF YOU NEED FULL INSTRUCTIONS TYPE F..FOR SHORT INSTRUCTIONS TYPE S"
271  PRINT : PRINT: PRINT : PRINT : PRINT : PRINT : PRINT : PRINT
272  INPUT A$
273  IF A$ = "S" THEN GOTO 500
274  IF A$ = "F" THEN GOTO 299
275  PRINT "ERROR..RETYPE": GOTO 272
299  FOR I = 1 to 30: PRINT : NEXT I
300  PRINT "     THIS STIMULATOR SYSTEM IS A CLOSED LOOP SYSTEM."
310  PRINT "AS SUCH, A SENSOR IS NECESSARY TO SHOW THE COMPUTER HOW MUCH STIMULATION"
320  PRINT "TO APPLY TO THE MUSCLE."
330  PRINT "THEREFORE, IN THIS PART OF THE PROGRAM, THE SENSOR MUST BE CHECKED."
340  PRINT "THE SENSOR IS TESTED BY FIRST PUTTING A KNOWN WEIGHT ON THE SENSOR"
350  PRINT "AND THEN SEEING THAT A PROPER DEFLECTION IS FOUND IN THE COMPUTER"
360  PRINT "NUMBERS WILL APPEAR ON THE COMPUTER THAT YOU MUST CHECK AFTER THE WEIGHT HAS BEEN PLACED ON."
390  PRINT : PRINT
391  PRINT "TYPE E TO CONTINUE": INPUT A$
392  IF A$ = "E" THEN GOTO 500
393  PRINT "ERROR..RETYPE": GOTO 391
500  FOR I = 1 to 30: PRINT : NEXT I
600  REM  TEST STRAIN GAUGES FOR OPERATION
610  REM  A GAUGE NUMBER MUST BE ASSIGNED TO A GIVEN GAUGE
620  REM  THIS GAUGE NUMBER MUST BE ASSIGNED AND BE BETWEEN 1 AND 10
640  FOR I = 1 TO 30: PRINT : NEXT I
650  PRINT "TURN STRAIN GAGE AMP ON"
660  PRINT : PRINT "ADJUST BALANCE FOR 125 UNITS"
670  PRINT "HIT ANY KEY WHEN ADJUSTED"
671  PRINT "ADJUST METER BALANCE AFTER COMPUTER BALANCE"
680  FOR I = 1 TO 10: PRINT : NEXT I
700  REM  700-800 LOOKS AT BALANCE FOR 125 UNITS
710  REM  STROBE A/D
720  POKE 49328,0
730  X = PEEK ( - 16384)
745  IF X > 127 THEN GOTO 800
```

```
 750  X = PEEK (49328)
 760  HTAB 1
 761  VTAB 22
 763  PRINT "     ";
 764  VTAB 22: HTAB 1
 765  PRINT X;
 790  GOTO 700
 800  POKE - 16368,0: REM   RESET KEYFLAG
 810  FOR I = 1 TO 30: PRINT : NEXT I
 820  PRINT "INPUT E FOR ERROR OR G TO GO ON"
 830  FOR I = 1 TO 10: PRINT : NEXT I
 840  INPUT A$
 850  IF A$ = "E" THEN GOTO 5000
 860  IF A$ = "G" THEN GOTO 900
 870  PRINT "INPUT ERROR..RETYPE"
 880  GOTO 840
 900  REM   CONTINUE CALIBRATION OF GAGE
 910  FOR I = 1 TO 30: PRINT : NEXT I
 920  PRINT "PLACE 5 LB LOAD ON THE SENSOR"
 930  PRINT : PRINT "INPUT SCALE FACTOR"
 940  INPUT SCALE
 950  IF SCALE > 10 THEN GOTO 6000
 960  IF SCALE < 1 THEN GOTO 6000
 970  PRINT "TYPE G WHEN WEIGHT IS ON"
 975  INPUT A$
 977  IF A$ = "G" THEN GOTO 1000
 990  PRINT "INPUT ERROR...RETYPE"
 995  GOTO 975
1000  POKE 49328,0
1010  FOR I = 1 to 10: NEXT I
1020  X = PEEK (49328)
1030  LET X = X - 125
1035  MICKEY = X
1040  X = X / SCALE
1050  FOR I = 1 to 30: PRINT : NEXT I
1060  PRINT "WEIGHT READS AS"
1070  PRINT : PRINT X; "POUNDS"
1100  FOR I = 1 TO 5: PRINT : NEXT I
1120  PRINT "IS THE WEIGHT CLOSE TO 5 LBS?"
1130  PRINT : PRINT "INPUT Y/N"
1140  INPUT A$
1150  IF A$ = "Y" THEN GOTO 1300
1160  IF A$ = "N" THEN GOTO 1200
1170  PRINT "INPUT ERROR...RETYPE"
1180  GOTO 1140
1200  FOR I = 1 to 30: PRINT : NEXT I
1210  PRINT "CALIBRATION ERROR"
1220  PRINT : PRINT "CHECK WIRING AND SCALE FACTOR"
1230  PRINT : PRINT "WAS SCALE "; SCALE
1240  PRINT : PRINT "Y/N ": INPUT A$
1245  IF A$ = "Y" THEN GOTO 1270
1250  IF A$ = "N" THEN GOTO 600
1270  GOTO 5170
1300  FOR I = 1 to 30: PRINT : NEXT I
1310  PRINT "TURN CONTROL AMP TO 0": PRINT "TYPE G TO GO ON"
1320  PRINT
```

```
1330   INPUT G$
1340   IF G$ = "G" THEN GOTO 1350
1345   PRINT "ERROR..RETYPE" : GOTO 1330
1350   PRINT "CONTROL AMP SET....GO ON"
1355   FOR I = 1 TO FELAY: NEXT I
1360   FOR I = 1 to 30: PRINT : NEXT I
1370   PRINT "SET THRESHOLD BY BRINGING"
1388   PRINT "GAIN UP UNTIL MUSCLE TWITCHES"
1390   PRINT "AND THEN HIT ANY KEY"
1400   PRINT : PRINT "START WITH VENTRAL MUSCLE"
1405   PRINT "TURNHIGH VOLTAGE ON..."
1406   PRINT "TYPE ANY KEY WHEN VOLTAGE ON"
1407   H = PEEK ( - 16384)
1408   IF H > 127 THEN GOTO 1410
1409   GOTO 1407
1410   POKE - 16368,0: PRINT "SET THRESHOLD NOW"
1411   REM
1412   FOR I = 1 to 10: PRINT : NEXT I
1413   PRINT ""
1420   X = 64
1430   POKE 49920,X
1431   HTAB 1: VTAB 22
1432   PRINT "      "
1433   VTAB 22: HTAB 1
1434   PRINT X
1436   PRINT "TYPE ANY KEY TO GO ON"
1440   X = PEEK ( - 16384)
1450   IF X > 127 THEN GOTO 1500
1460   GOTO 1420
1500   T1 = 64
1510   REM T1=THRESHOLD FOR VENTRAL MUSCLE
1520   POKE - 16368,0
1530   FOR I = 1 to 30: PRINT : NEXT I
1535   POKE 49220,0
1540   PRINT "THRESHOLD FOR MUSCLE 1 WAS"
1550   PRINT T1
1560   PRINT : PRINT : PRINT "SET MUSCLE 2"
1570   PRINT "TYPE G TO GO ON" : INPUT 6$
1571   IF G$ = "G" THEN GOTO 1580
1573   PRINT "ERROR..RETYPE" : GOTO 1570
1580   X = 64
1581   REM
1582   FOR I = 1 to 30: PRINT : NEXT I
1590   PRINT "BEGIN": PRINT ""
1595   FOR I = 1 TO 10: PRINT : NEXT I
1600   X = 64
1601   IF X > 85 THEN LET X = 85
1620   POKE 49922,X
1630   HTAB 1: VTAB 22
1640   PRINT "       "
1650   VTAB 22: HTAB 1
1660   PRINT X
1670   X = PEEK ( - 16384)
1680   IF X > 127 THEN GOTO 1800
1690   GOTO 1600
1800   POKE - 16368,0
```

```
1810    T2 = 64
1820    REM   T2=THRES 2
1830    POKE 49922,0
1840    FOR I = 1 to 30: PRINT : NEXT I
1850    PRINT "THRESHOLD FOR MUSCLE 2 WAS"
1860    PRINT T2
1870    FOR I = 1 to 10: PRINT : NEXT I
1890    FOR I = 1 TO FELAY: NEXT I
1900    IF T1 > MAX OR T2 > MAX THEN GOTO 8000
1910    FOR I = 1 to 30: PRINT : NEXT I
2000    PRINT "CHECK BLOOD PRESSURE AND HEART"
2010    PRINT "RATE FOR SAFE LIMITS AND TYPE"
2020    PRINT "G TO GO ON"
2030    FOR I = 1 TO 10: PRINT : NEXT I
2040    INPUT A$
2050    IF A$ = "G" THEN GOTO 2100
2060    PRINT "INPUT ERROR...RETYPE"
2070    GOTO 2040
2100    GOTO 3000
3000    REM CALCULATE SCALE FACTORS FOR T1 and T2
3010    REM
3020    I1 = T1:I2 = T2
3030    WANT = 1
3050    G1 = 50
3060    REM   WAIT=STIM DELAY   G1=LOOP 4 SEC STIM
3100    FOR I = 1 TO 30: PRINT : NEXT I
3110    PRINT "THE EXERCISE IS READY TO START"
3120    PRINT "CHECK ALL ELECTRODES AND WIRES"
3130    PRINT : PRINT "WHAT IS THE MAXIMUM TENSION"
3140    PRINT "ON VENTRAL AND DORSAL MUSCLES"
3150    INPUT VENT,DS
3170    IF VENT > 30 OR DS > 30 THEN GOTO 9000
3180    DF1 = (VENT/5) * MICKEY
3181    DA2 = (DS/5) * MICKEY
3200    FOR I = 1 to 30: PRINT : NEXT I
3205    POKE 49920,0: POKE 49922,0
3210    PRINT "TYPE R WHEN READY TO START"
3220    PRINT "HIT ANY KEY TO STOP SEQUENCE"
3225    FOR I = 1 TO 10: PRINT : NEXT I
3226    D6 = 0
3230    INPUT A$
3231    OFF = 0
3240    IF A$ = "R" THEN GOTO 3300
3250    PRINT "INPUT ERROR..RETYPE"
3260    GOTO 3230
3300    DUCK = 2.5 * T1
3301    DUCK = (DUCK - T1)/50
3302    GOOSE = 2.5 * T2
3303    GOOSE = (GOOSE - T2)/50
3305    D6 = D6 + 1: HTAB 1: VTAB 22: PRINT "        "
3306    HTAB 1: VTAB 22
3307    PRINT D6
3308    I1 = T1
3309    I2 = T2
3310    FOR I = 1 to G1
3311    POKE 49328,0
```

```
3312    I2 = T2
3313    FOR H = 1 TO WANT : NEXT H
3320    POKE 49922,I1
3321    POKE 49921,0
3322    D = PEEK (49328)
3323    IF (- 1 *DF1) - (D-125) <  0 THEN GOTO 3327
3325    LET Y = I1 + DUCK
3326    GOTO 3330
3327    Y = I1
3330    IF Y < 200 THEN LET I1 = Y
3340    X = PEEK ( - 16384)
3350    IF  > 127 THEN GOTO 1
3360    REM
3370    NEXT I
3410    FOR I = 1 to G1
3411    POKE 49328,0
3412    I1 = T1
3413    FOR H = 1 TO WANT : NEXT H
3420    POKE 49922,I2
3421    POKE 49920,0
3422    D = PEEK (49328)
3423    IF (- 1 * DA2) + (D - 125) <  0 THEN GOTO 3427
3425    Y = I2 + GOOSE
3426    GOTO 3430
3427    Y = I2
3430    IF Y < 200 THEN LET I2 = Y
3440    X = PEEK ( - 16384)
3450    IF X >127 THEN GOTO 1
3460    REM
3461    REM
3470    NEXT I
3500    REM   4 SEC WAIT
3501    FOR I = 1 TO FELAY : NEXT I
3502    REM
3503    REM
3504    REM
3510    POKE 49920,2: POKE 49922,0
3520    REM
3600    FOR I = 1 TO FELAY : NEXT I
3610    GOTO 3300
4999    END
5000    REM   THIS IS A ROUTINE IF SENSOR IS WRONG OR
        WILL NOT ADJUST
5010    FOR I = 1 TO 30: PRINT : NEXT I
5020    PRINT "PLEASE DO THE FOLLOWING.."
5030    PRINT
5040    PRINT "         1.CHECK WIRING FROM"
5050    PRINT "             METER TO COMPUTER"
5060    PRINT "         2. FIND OUT IF BALANCE"
5070    PRINT "             ADJUSTS METER"
5080    PRINT : PRINT "IF BALANCE WORKS AND COMPUTER
        DOESNT RESPOND"
5111    PRINT "CHANGE A/D BOARD AND REBOOT"
5120    PRINT : PRINT "IS PROBLEM OVER (Y/N)"
5130    INPUT A$
5140    IF A$ = "Y" THEN GOTO 600
```

```
5145   FOR I = 1 TO 30: PRINT : NEXT I
5150   REM   TRY SOMETHING ELSE
5160   PRINT : PRINT "CHECK WIRES FROM STRAIN GAGE TO
       METER FOR POLARITY AND COLOR CODE"
5170   PRINT "CHECK BATTERIES IN STRAIN GAGE AMP"
5200   PRINT : PRINT "IS PROBLEM OVER (Y/N)"
5210   INPUT A$
5220   IF A$ = "Y" THEN GOTO 600
5230   PRINT "STOP UNTIL PROBLEM IS OVER"
5240   GOTO 5200
6000   PRINT "VARIABLE IS TOO LARGE OR SMALL"
6010   PRINT : PRINT "    RETYPE"
6020   GOTO 940
8000   FOR I = 1 to 30: PRINT : NEXT I
8010   PRINT "THRESHOLD WAS TOO HIGH ON"
8020   IF T1 > MAX THEN GOTO 8100
8030   PRINT "DORSAL MUSCLE GROUP"
8040   GOTO 8200
8100   PRINT "VENTRAL MUSCLE GROUP"
8200   PRINT : PRINT "CHECK FOR BAD ELECTRODE"
8210   PRINT "OR LOOSE WIRE"
8230   PRINT : PRINT : PRINT "DID YOU FIND A PROBLEM?"
8235   PRINT "ANSWER Y/N"
8240   INPUT A$
8245   IF A$ = "Y" THEN GOTO 1300
8250   IF A$ = "N" THEN GOTO 8400
8400   FOR I = 1 TO 30: PRINT : NEXT I
8410   GOTO 8230
9000   FOR I = 1 TO 30: PRINT : NEXT I
9010   PRINT "THE TARGET MUST NEVER EXCEED 30 LBS"
9020   PRINT "PLEASE TRY AGAIN"
9030   GOTO 3100
9500   POKE - 16368,0
9510   GOTO 3200
10000  POKE 49920,0: POKE 49922,0
10005  PRINT "DORSAL MUSCLE WAS ONLY"
10010  PRINT (125 - D) / SCALE, "POUNDS END RUN"
10015  REM
10020  GOTO 10015
10100  POKE 49920,0: POKE 49922,0
10105  PRINT "VENTRAL MUSCLE STRENGTH WAS ONLY"
10110  PRINT (D - 125) / SCALE;" POUNDS...END RUN"
10115  REM
10120  GOTO 10115
```

I claim:

1. A therapy system for a human being comprising:
a stimulation generator for generating electrical signals of muscle stimulating amplitude and waveform,
surface electrode means in electrical communication with said stimulation generator for applying said electrical signals to the skin of said human being at a location providing stimulating access to a muscle connected for causing movement of a joint of said human being,
restraining means attached to said joint for restraining movement thereof and generating a load signal corresponding to the actual load being applied to said joint by said muscle;
load selection means for selecting a target load for said muscle, and
control means in electrical communication with said stimulation generator for controlling the operation of said stimulation generator to cause alternating stimulation and resting of said muscle; said control means also being in electrical communication with said restraining means and said load selection means for periodically adjusting said stimulation in accordance with the difference between said target load and said actual load to cause isometric muscle effort at a level near the value of said target load.

2. A therapy system for a human being comprising:
a stimulation generator for generating electrical signals of muscle stimulating amplitude and waveform,
surface electrode means in electrical communication with said stimulation generator for applying said electrical signals to the skin of said human being at a location providing stimulation access to a muscle connected for causing movement of a joint of said human being,
an articulated brace attached to said joint for articulating movement with movement of said joint,
a load cell mounted upon said brace for substantially inhibiting said movement and generating a load signal corresponding to the load being applied by said muscle to said joint,
load selection means for selecting a target load for said muscle, and
control means in electrical communication with said load cell and said load selection means; said control means being responsive to said load signal for controlling the operation of said stimulation generator to cause controlled isometric exercising of said muscle at a level specified by said load selection means.

3. A leg brace comprising:
a rigid upper leg section for attachment to the upper portion of a human leg,
a rigid lower leg section for attachment to the lower portion of said leg and hingedly connected to said upper leg section along a hinge line coinciding with the line of rotation of the knee joint of said leg,
a rigid foot section for attachment to the foot of said leg and hingedly connected to said lower leg section along a hinge line coinciding with the line of rotation of the ankle joint of said leg,
a first load cell mounted upon said leg brace for substantially preventing rotational movement between said upper leg section and said lower leg section and generating a feedback signal indicating a rotational load exerted by said leg at said knee joint, and
a second load cell mounted upon said leg brace for substantially preventing rotational movement between said lower leg section and said foot section and generating a feedback signal indicating a rotational load exerted by said leg at said ankle joint.

4. A leg brace according to claim 3 wherein said first load cell maintains said leg in a position such that it is slightly bent at the knee.

5. A leg brace according to claim 4 wherein said upper leg section and said lower leg section each comprise a plurality of longitudinally extending framing rods which are adjustably joined to permit adjustment of the length of their associated leg sections.

6. Physical therapy apparatus comprising:
a rigid upper leg section for attachment to the upper portion of a human leg,
a rigid lower leg section for attachment to the lower portion of said leg and hingedly connected to said upper leg section along a hinge line coinciding with the line of rotation of the knee joint of said leg,
a rigid foot section for attachment to the foot of said leg and hingedly connected to said lower leg section along a hinge line coinciding with the line of rotation of the ankle joint of said leg,
a first load cell interconnecting said upper leg section and said lower leg section for substantially preventing rotational movement therebetween and generating a first feedback signal indicating a rotational load exerted by said leg at said knee joint,
a second load cell interconnecting said lower leg section and said foot section for substantially preventing rotational movement between said lower leg section and said foot section and generating a second feedback signal indicating a rotational load exerted by said leg at said ankle joint,
muscle stimulation means for stimulation of said leg to cause rotation effort said knee joint and said ankle joint,
control means in electrical communication with said load cells and said stimulation means for reception of said first feedback signal and said second feedback signal and responsive thereto for causing said stimulation means to stimulate said leg to exert a rotation effort corresponding to a predetermined target load.

7. Apparatus according to claim 6 wherein said first load cell maintains said upper leg section and said lower leg section at relative positions such that said leg is slightly bent at the knee.

8. Apparatus according to claim 7 wherein said upper leg section and said lower leg section each comprise a plurality of longitudinally extending framing rods which are adjustably joined to permit adjustment of the length of their associated leg sections.

9. Therapy method for a human being comprising the steps of:
applying a transcutaneous electrode to the skin of said human above a muscle connected for moving a joint of said human,
attaching to said joint a brace which substantially restricts movement thereof,
stimulating isometric exertion of said muscle against said brace by applying an electrical stimulation signal to said electrode,
measuring the effort exerted by said muscle against said brace,
adjusting said stimulation signal until said effort reaches a predetermined target load,
interrupting said stimulating step to rest said muscle, and
repeating said stimulating, measuring, adjusting, and interrupting steps.

10. Therapy method according to claim 9 wherein said repeating of said steps is continued until said stimulation signal reaches a predetermined maximum value indicating exhaustion of said muscle.

11. Therapy method according to claim 10 wherein said stimulating step and said interrupting step each have predetermined durations.

12. Physical therapy apparatus comprising:
a leg brace for substantially inhibiting angular motion of the knee joint and the ankle joint of a human leg to which said brace is attached,
muscle stimulation means for mounting upon said leg to stimulate rotation effort at said joints, first feedback means mounted upon said brace for generating a first feedback signal indicating the rotation effort by said leg at said knee joint,
second feedback means mounted upon said brace for generating a second feedback signal indicating the rotation effort by said leg at said ankle joint, and
control means in electrical communication with said first feedback means, said second feedback means and said muscle stimulation means for causing adjustment of the stimulation activity of said muscle stimulation means until said feedback signals indicate that said rotation efforts are at predetermined target levels.

* * * * *